(12) United States Patent
Van Der Schaar et al.

(10) Patent No.: US 8,982,329 B2
(45) Date of Patent: Mar. 17, 2015

(54) METHOD AND APPARATUS FOR MEASURING LINE END SHORTENING, SUBSTRATE AND PATTERNING DEVICE

(75) Inventors: Maurits Van Der Schaar, Eindhoven (NL); Arie Jeffrey Den Boef, Walre (NL); Richard Johannes Franciscus Van Haren, Waalre (NL); Marcus Adrianus Van De Kerkhof, Helmond (NL)

(73) Assignee: ASML Netherlands B.V., Veldhoven (NL)

( * ) Notice: Subject to any disclaimer, the term of this patent is extended or adjusted under 35 U.S.C. 154(b) by 902 days.

(21) Appl. No.: 12/933,806

(22) PCT Filed: Apr. 22, 2009

(86) PCT No.: PCT/EP2009/002915
§ 371 (c)(1),
(2), (4) Date: Dec. 20, 2010

(87) PCT Pub. No.: WO2009/130010
PCT Pub. Date: Oct. 29, 2009

(65) Prior Publication Data
US 2011/0109888 A1 May 12, 2011

Related U.S. Application Data

(60) Provisional application No. 61/071,360, filed on Apr. 24, 2008.

(51) Int. Cl.
*G03B 27/32* (2006.01)
*G01B 11/14* (2006.01)
*G03F 7/20* (2006.01)
*G01N 21/956* (2006.01)
*G03F 1/00* (2012.01)
*G03F 1/44* (2012.01)

(52) U.S. Cl.
CPC ...... *G03F 7/70683* (2013.01); *G01N 21/95607* (2013.01); *G03F 1/14* (2013.01); *G03F 1/44* (2013.01); *G03F 7/70625* (2013.01); *G03F 1/0092* (2013.01)
USPC ............................................ 355/77; 356/625

(58) Field of Classification Search
USPC ............................................ 355/77; 356/625
See application file for complete search history.

(56) References Cited

U.S. PATENT DOCUMENTS

| 2002/0182516 | A1 | 12/2002 | Bowes |
| 2004/0190008 | A1* | 9/2004 | Mieher et al. ................. 356/625 |
| 2005/0089775 | A1 | 4/2005 | Archie et al. |

FOREIGN PATENT DOCUMENTS

| EP | 1 628 164 A2 | 2/2006 |
| EP | 1 739 491 A1 | 1/2007 |

OTHER PUBLICATIONS

International Search Report mailed Aug. 11, 2009 for International Application No. PCT/EP2009/002915, 5 pgs.
Hung K et al., "Scatterometry Measurements of Line End Shortening Structures for Focus-Exposure Monitoring", Proceedings of SPIE—The International Society for Optical Engineering—Metrology, Inspection, and Process Control for Microlithography XX, 2006, SPIE US, vol. 6152 I.
Hannon S et al., "Cost Effective CD Control for DUV Implant Layers Using the Archer MPX Focus-Exposure Monitor", Progress in Biomedical Optics and Imaging—Proceedings of SPIE—Metrology, Inspection, and Process Control for Microlithography XIX 2005, SPIE US, vol. 5752, No. III, pp. 1127-1136.

* cited by examiner

*Primary Examiner* — Peter B Kim
*Assistant Examiner* — Michelle Iacoletti
(74) *Attorney, Agent, or Firm* — Sterne, Kessler, Goldstein & Fox P.L.L.C.

(57) ABSTRACT

End of line effect can occur during manufacture of components using a lithographic apparatus. These end of line effects can result in line end shortening of the features being manufactured. Such line end shortening may have an adverse impact on the component being manufactured. It is therefore desirable to predict and/or monitor the line end shortening. A test pattern is provided that has two separate areas such that, as designed, when the two areas are illuminated with radiation (for example from an angle-resolved scatterometer) they result in diffused radiation with asymmetry that is equal in sign to each other, but opposite in magnitude. When the test pattern is actually manufactured, line end shortening occurs, and so the asymmetry of the two areas are not equal and opposite. From the measured asymmetry of the manufactured test pattern, the amount of line end shortening that has occurred can be estimated.

13 Claims, 8 Drawing Sheets

METHOD AND APPARATUS FOR MEASURING LINE END SHORTENING, SUBSTRATE AND PATTERNING DEVICE

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

In the manufacture of components using a lithographic apparatus, end of line (EOL) effects can occur. These end of line effects can result in a component feature (such as a channel or gate) that is intended to have a square end being manufactured with a non-square end, such as a tapered, curved, or rounded end.

Typically, a feature of a component being manufactured using a lithographic apparatus is designed to have a length which meets a certain requirement. If the end of line effects described above occur, then the length of the feature can become smaller than the design requirement towards the end of the feature. Where this occurs, the feature effectively becomes shorter than intended. This phenomenon is known as line end shortening (LES), and can have an adverse effect on the component.

For example, in the manufacture of channels for a transistor, the length of the channel is crucial to transistor performance. Thus, if the channel length becomes less than the design requirement due to the end of line effects described above, then the channel effectively becomes shorter, and the transistor performance is affected.

In some instances, it is possible to account for line end shortening that will occur in the manufacturing process during the design process. However, this may require a knowledge of the line end shortening that is likely to occur for particular features in the design. Such knowledge of the extent of line end shortening may be difficult and time consuming to obtain. For example, current methods involve the use of a scanning electron microscope, which is both slow and expensive.

It may also be useful to know the amount of line end shortening that has actually occurred on a particular substrate. For example, it would be useful to know the actual amount of line end shortening that has occurred compared with the amount predicted. This could be used, for example, to verify whether the amount of line end shortening that was predicted to occur during design of a pattern has actually occurred on each substrate. Again, current methods are prohibitively slow and/or expensive.

SUMMARY

It is desirable to provide a method for determining the extent of line end shortening that occurs is likely to occur during exposure of a substrate that is quick, inexpensive and/or simple to perform. It is also desirable to provide apparatus for performing such methods.

According to an aspect of the invention, there is provided a method of measuring line end shortening of features on a substrate, the method including illuminating the test pattern provided on a substrate with a radiation beam; collecting radiation scattered by the illuminated test pattern; detecting asymmetry of the scattered radiation beam; and determining, from the asymmetry of the scattered radiation beam, the amount of line end shortening of the features.

According to another aspect of the invention, there is provided a substrate for use in measuring line end shortening, the substrate having provided thereon a pattern which, when not subjected to any line end shortening, includes a first repeating pattern and a second repeating pattern, wherein: the first repeating pattern is arranged to scatter a radiation beam such that the scattered radiation beam has a first asymmetry; and the second repeating pattern is arranged to scatter a radiation beam such that the scattered radiation beam has a second asymmetry that is substantially equal in magnitude but opposite in sign to the first asymmetry.

According to another aspect of the invention, there is provided a patterning device configured to expose a pattern on a substrate, which pattern, excluding line end shortening effects, includes a first repeating pattern and a second repeating pattern, wherein: the first repeating pattern is arranged to scatter a radiation beam such that the scattered radiation beam has a first asymmetry; and the second repeating pattern is arranged to scatter a radiation beam such that the scattered radiation beam has a second asymmetry that is equal in magnitude but opposite in sign to the first asymmetry.

According to another aspect of the invention, there is provided a measurement system for measuring the length of line end shortening of features on a substrate that has provided thereon a test pattern which, when not subjected to any line end shortening, includes a first repeating pattern and a second repeating pattern, wherein: the first repeating pattern is arranged to scatter the radiation beam such that the scattered radiation beam has a first asymmetry; and the second repeating pattern is arranged to scatter the radiation beam such that the scattered radiation beam has a second asymmetry that is equal in magnitude but opposite in sign to the first asymmetry, the measurement system including: a radiation device configured to irradiate the substrate with a radiation beam; a collector configured to collect radiation from the radiation device that has been scattered by the substrate; a detector configured to detect asymmetry of the scattered radiation beam; and a controller configured to calculate line end shortening from the detected asymmetry of the first and second repeating patterns.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
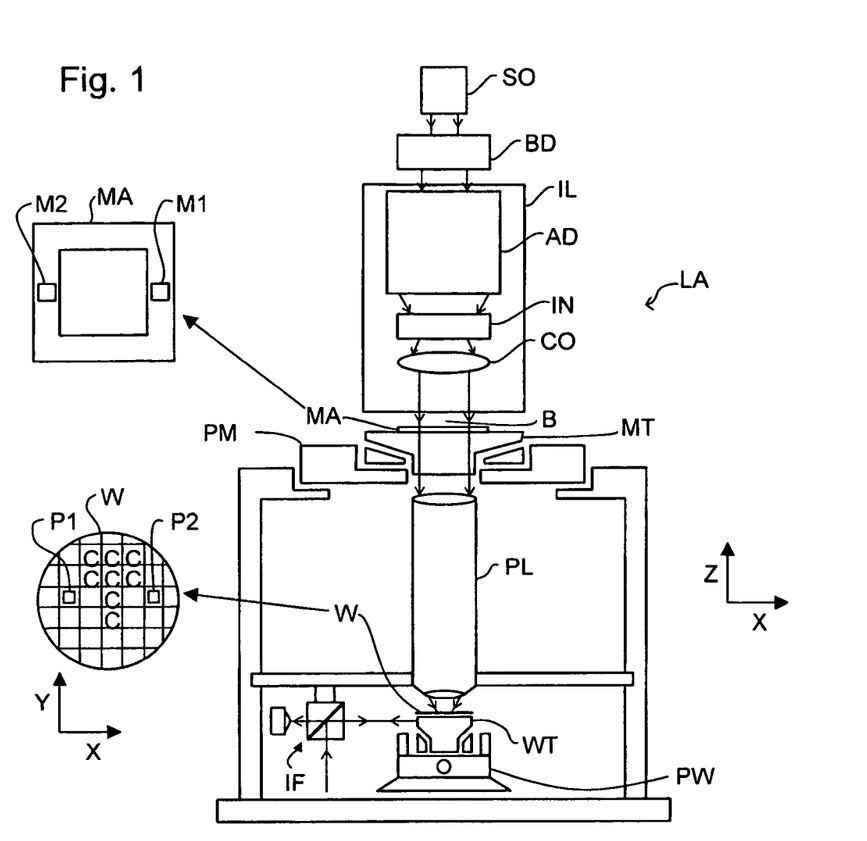
FIG. 1 depicts a lithographic apparatus in accordance with an embodiment of the invention.

FIG. 1 schematically depicts a lithographic apparatus. The apparatus includes an illumination system (illuminator) IL configured to condition a radiation beam B (e.g. UV radiation or DUV radiation); a patterning device support or support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, to direct, shape, or control radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate.

An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the patterning device support (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device (e.g. mask) MA with respect to the path of the radiation beam B, e.g. after mechanical retrieval from a mask library, or during a scan. In general, movement of the patterning device support (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g. mask table) MT may be connected to a short-stroke actuator only, or may be fixed. Patterning device (e.g. mask) MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the mask alignment marks may be located between the dies.

The depicted apparatus could be used in at least one of the following modes:

1. In step mode, the patterning device support (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g. mask table) MT and the substrate table WT are scanned synchronously while a pattern imparted to the radiation beam is projected onto a target portion C (i.e. a single dynamic exposure). The velocity and direction of the substrate table WT relative to the patterning device support (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
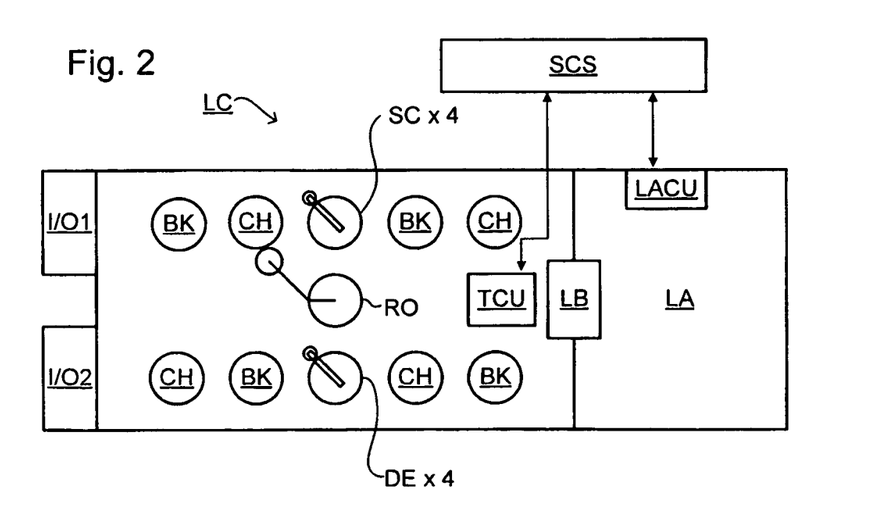
FIG. 2 depicts a lithographic cell or cluster in accordance with an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
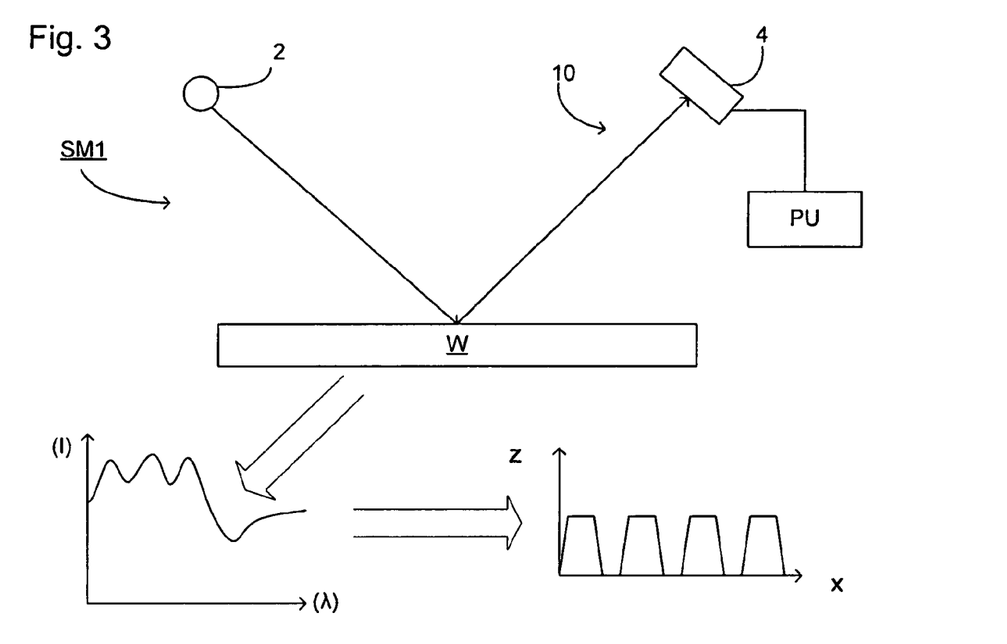
FIG. 3 depicts a scatterometer in accordance with an embodiment of the invention.

FIG. 3 depicts a scatterometer SM1 which may be used in an embodiment of the present invention. It includes a broadband (white radiation or light) radiation projector 2 which projects radiation onto a substrate W. The reflected radiation is passed to a spectrometer detector 4, which measures a spectrum 10 (intensity (I) as a function of wavelength (λ)) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
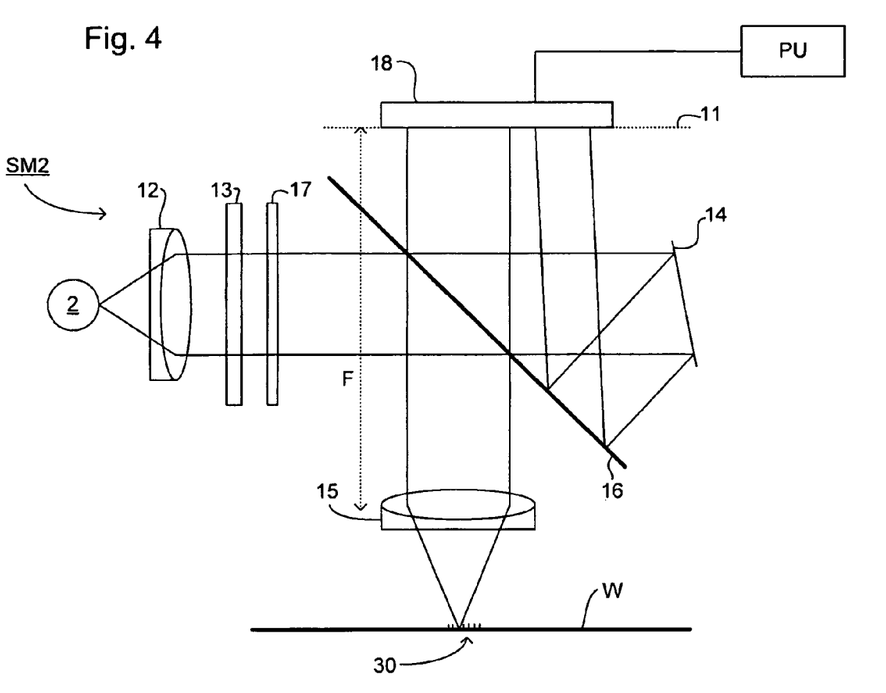
FIG. 4 depicts a scatterometer in accordance with an embodiment of the invention.

Another scatterometer SM2 that may be used with an embodiment of the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than including a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband radiation source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$, and a spacing of at least $2\delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

In the manufacture of ICs, end of line (EOL) effects can result in features being manufactured differently to the intended design. In particular, line end shortening (LES) can occur, leading to a reduction of the effective extent of the feature.

Figure 5:
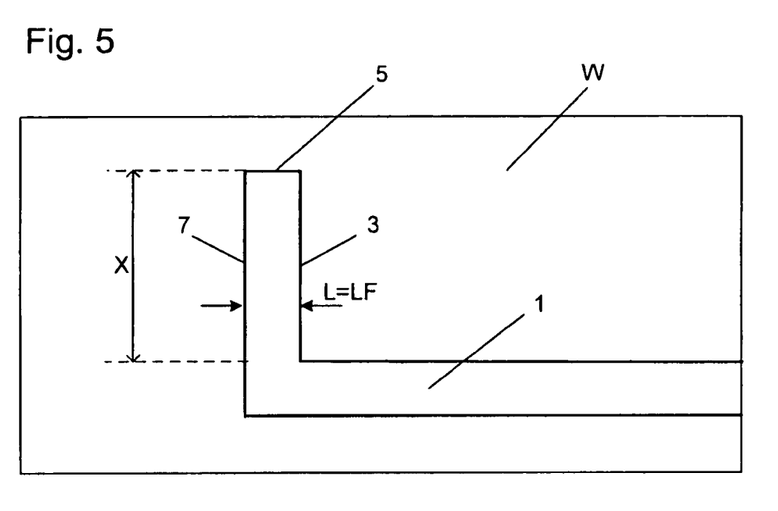
FIG. 5 depicts a typical feature on a substrate as designed i.e. a feature having being subjected to no end of line effects.

A typical feature (or gate) 10 that may be formed on a substrate W is shown in FIG. 5. The feature 10 shown in FIG. 5 has the shape and size of the feature as designed (i.e. having experienced no end of line effects). The feature 1 in FIG. 5 can form a part of any feature, gate, or device produced on a substrate W. For example, the feature, device, or gate 1 could form part of a transistor.

The feature 1 as designed has square corners at its end 5. In other words, the end surface 5 is perpendicular to the two adjacent side surfaces 3, 7.

The minimum gate length of the features on a substrate W is typically determined by the technology node. In the example shown in FIG. 5, the technology node length LF (which may also be referred to as the critical dimension (CD))

is equal to the length L of the feature 1 all of the way along the feature 1, including at its end 1.

Figure 6:
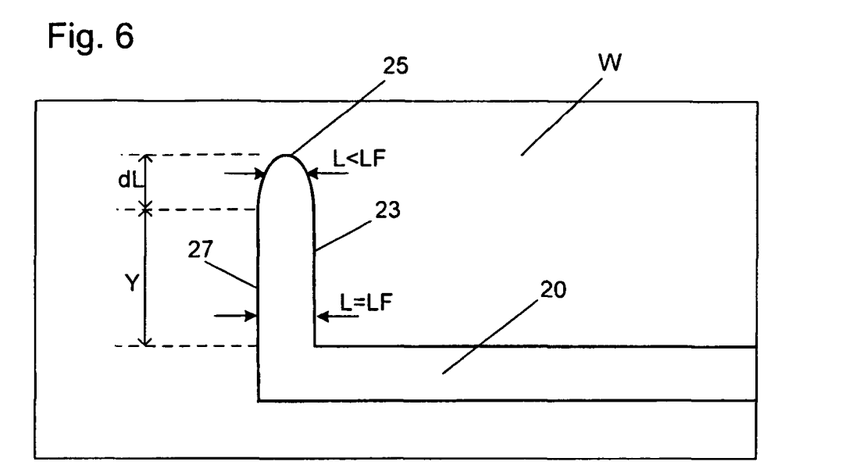
FIG. 6 depicts the feature on the substrate shown in FIG. 5 as manufactured, i.e. the feature of FIG. 5 having experienced end of line effects.

FIG. 6 shows a typical feature 20 as actually manufactured on a substrate W. The feature 20 shown in FIG. 6 is intended, or designed, to be the same as the feature 1 shown in FIG. 5. However, as a result of end of line effects during manufacture, the end 25 of feature 20 shown in FIG. 6 is very different to the equivalent end 15 of feature 10 shown in FIG. 5. In particular, whereas the end 5 of the feature 1 in FIG. 5 is perpendicular to the side surfaces 3, 7, the end 25 of the feature 20 in FIG. 6 is a tapered, rounded, and/or curved surface between the two side surfaces 23, 27. As such, between the end of side surface 23, and the end of side surface 27, the length L of the manufactured feature 20 is less than the design requirement (which could be the technology node length) LF. As such, the extent of the feature, or gate, 1 over which the feature length L meets the design requirement LF, is reduced (by a value dL) from a value X for the feature 1 as designed, to a value Y for a feature 20 as manufactured. This phenomenon is known as line end shortening (LES). In other words, LES refers to the reduction in the extent over which the length of a feature, or gate, 1, 20 meets its design requirement.

Failure to meet the design requirement (L=LF) can have significant effect on the performance of the gate, component and/or integrated circuit. Thus, end of line effects, and resulting line end shortening, need to be carefully monitored. This enables them to be, for example, accounted for and/or compensated for in the design process.

Figure 7:
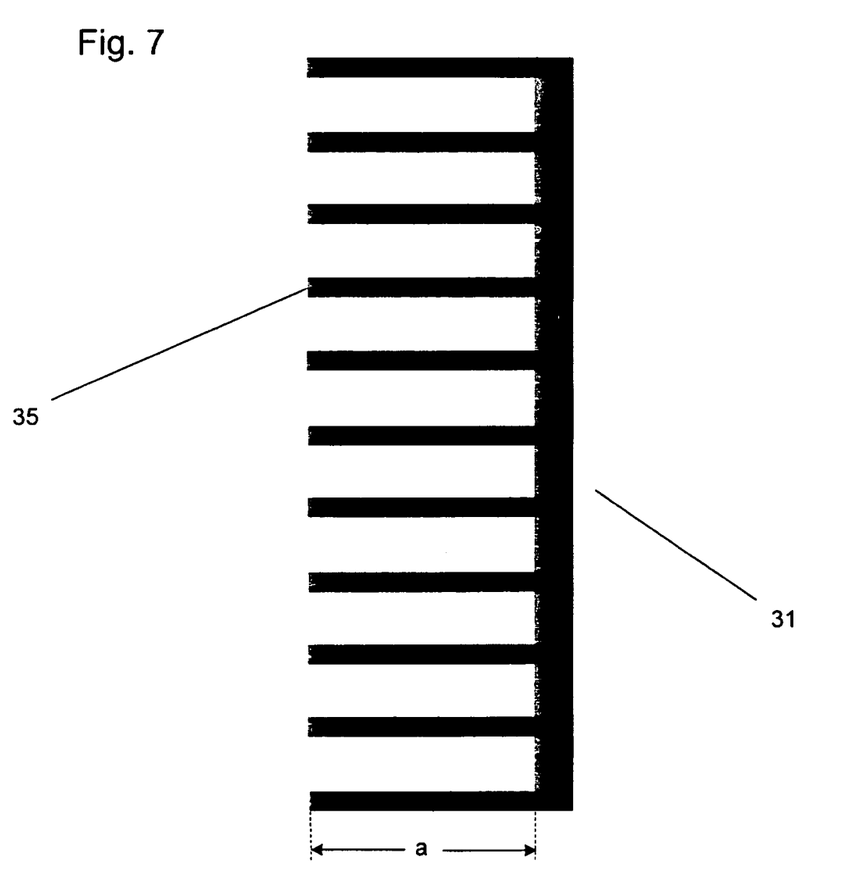
FIG. 7 depicts a comb-like structure that could be produced on a substrate as designed i.e. having experienced no end of line effects.
Figure 8:
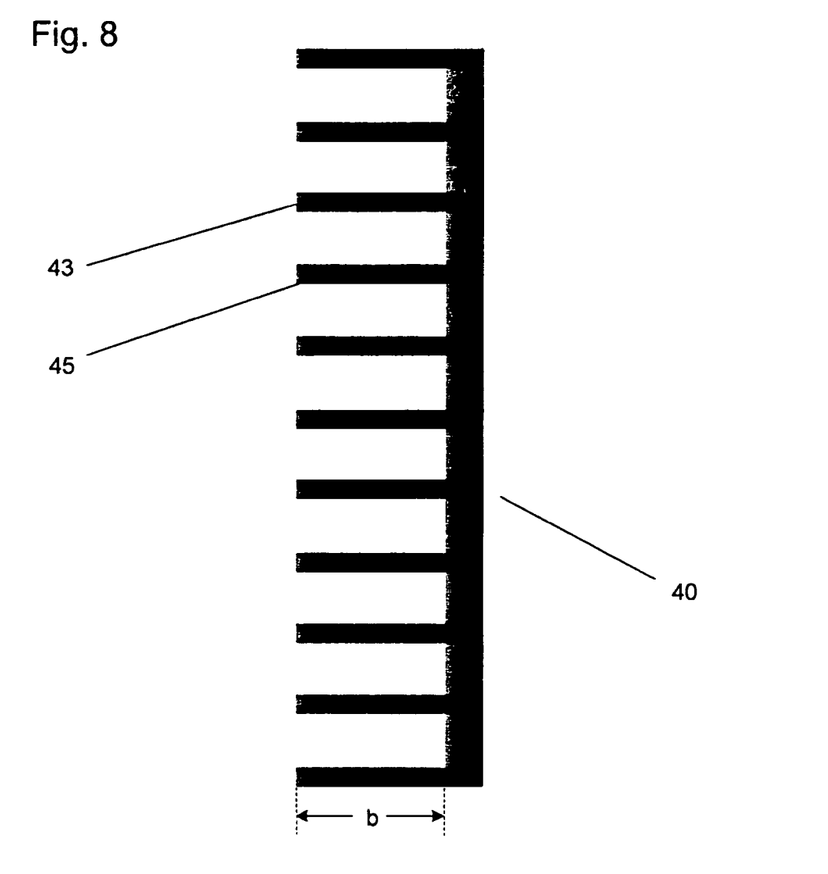
FIG. 8 depicts a comb-like structure which has smaller teeth than those of the comb-like structure shown in FIG. 7 due to end of line effects leading to line end shortening and thereby reducing the effective length of the teeth.

FIGS. 7 and 8 show the effect of line end shortening on a comb-like structure on a substrate. FIG. 7 shows a comb-like structure 31 with teeth 35 as designed. The teeth 35 as designed have a length a. The comb-like structure 40 shown in FIG. 8 shows how the effective length a of the teeth 35 of the comb-like structure shown as designed in FIG. 7 is reduced to become length b of teeth 45. This reduction is due to line end shortening during manufacture. In FIG. 8, the precise details of the ends 43 of teeth 45 are not shown in detail. Typically, the ends 43 would be rounded, tapered, and/or curved as in the case of the ends 25 of feature 20 shown in FIG. 6. However, the ends 43 depicted in FIG. 8 for comb-like structure 40 show the extent of the effective length b of the teeth 45 after line end shortening. For example, the end 43 of the teeth 45 shown in FIG. 8 could represent the point at which the teeth 45 become narrower than the design requirement (such as the technology node size or critical dimension) LF.

According to the illustrated embodiment, the line end shortening effect shown in FIGS. 7 and 8 is used in a test pattern on a substrate in order to infer, calculate, predict and/or estimate the amount of line end shortening that is likely to be experienced on the features (for example critical features) on a given substrate of interest. The substrate of interest could, for example, form at least a part of an IC.

Figure 9:
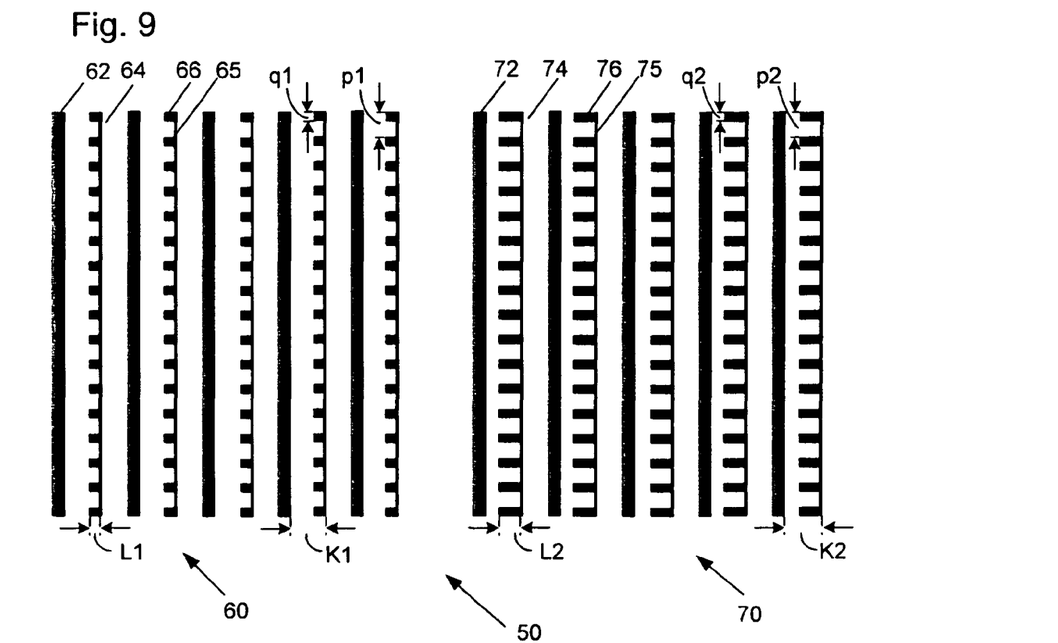
FIG. 9 depicts a pattern for use on a substrate for estimating line end shortening according to an embodiment of the invention.

FIG. 9 shows an example of a test pattern for use in an embodiment of the present invention. The pattern 50 shown in FIG. 9 is the pattern to be provided on a substrate as designed. As such, the pattern shown in FIG. 9 has not been subjected to any end of line effects, such as line end shortening. The measurement systems of FIGS. 3 and 4 are configured to determine the asymmetry of the pattern 50 to predict the amount of line end shortening.

The test pattern 50 could be provided on a test substrate in order to predict the amount of line end shortening that is likely to occur on a substrate of interest that is to be subsequently manufactured. This prediction could be used, for example, to adjust the design of the pattern on the substrate of interest to take line end shortening into account.

Alternatively, or additionally, the test pattern 50 could be provided on the substrate of interest itself, for example on a substrate that will result in at least a part of a component. For example, the test pattern 50 could be provided in spare areas on a substrate of interest, such as in one or more scribe lanes. The test pattern could thus be incorporated into each and every substrate manufactured, or a given percentage of them. In this way, the amount of line end shortening that has occurred on each substrate could be measured, estimated, and/or calculated. The actual amount of line end shortening could then be compared with the predicted amount of line end shortening, thereby checking the accuracy of each of the manufactured substrates.

The pattern 50 shown in FIG. 9 includes two separate areas, 60, 70. The separate areas 60, 70 each have alternating features.

The first area 60 includes solid lines 62 and comb-like structures 64. The solid lines 62 and the comb-like structures 64 are alternating throughout area 60 of test pattern 50. The comb-like structures 64 include a solid line 65 from which teeth 66 extend, or protrude. The teeth 66 can extend, or protrude, perpendicularly from the solid line 65. Furthermore, the teeth 66 can all protrude from the same side of solid line 65. Still further, the teeth 66 can be regularly spaced with a pitch p1. Also in the embodiments shown in FIG. 9, the teeth all have substantially the same width q1 (for the avoidance of doubt, the width q1 as depicted in FIG. 9 is analogous to the length L of the gates 1, 20 shown in FIGS. 5 and 6). Furthermore, the teeth 66 can all have the same length of protrusion L1 from the solid line 65.

The second area 70 of test pattern 50 of the embodiment shown in FIG. 9 also includes a regular, repeating, pattern including alternating solid lines 72 and comb-like structures 74. According to the embodiment shown in FIG. 9, the comb-like structure 74 also includes a solid line 75 with protruding teeth 76. The protruding teeth 76 have a pitch p2, a width q2 and a length L2. In the embodiment shown in FIG. 9, the pitch p2 of the teeth 76 of second area 70 is equal to the pitch p1 of the teeth 66 of first area 60, and the width q2 is equal to the width q1 of the teeth 66 of the first area 60. However, the length L2 of the teeth 76 of the second area 70 is greater than the length L1 of the teeth 66 of first area 60.

In other embodiments, the pitch p1 of the teeth 66 of first area 60 need not be equal to the pitch p2 of the teeth 76 of the area 70. In still other embodiments, the width q1 of the teeth 66 of area 60 need not be equal to the width q2 of the teeth 76 of the second area 70.

Although the structures including solid lines 65, 75, with protruding teeth 66, 76 have been referred to as comb-like structure 64, 74 herein, they may also be referred to as crenellations. Thus, the structures 64, 74 that alternate with solid lines 62, 72 in the first and second areas 60, 70 of the test pattern 50 may be referred to as being crenellated.

In the test pattern 50 shown in FIG. 9, the size and/or shape of the structures, in particular the comb-like structures 64, 74, are chosen so as to be representative of the feature sizes (such as the critical dimension and/or the technology node dimension) of the actual substrate of interest for which the line end shortening is to be inferred, predicted, calculated and/or estimated. For example, the pitch p1, p2, width q1, q2, and/or length L1, L2 of the teeth 66, 76 of the two areas 60, 70 of repeating patterns can be chosen so as to be representative of the feature sizes of the substrate of interest. For example, the pitch p1, p2, width q1, q2, and/or length L1, L2 could be chosen to be the same as, or similar to, those of the features of the substrate of interest.

According to the embodiments shown in FIG. 9, the length L1, L2 of the teeth, 66, 76 and/or the spacing K1, K2 between the comb-like structures 64, 74 and the solid lines 62, 72 are chosen such that the asymmetry of area 60 has a value that is substantially the same in magnitude as the asymmetry of the area 70, but oppose in sign. In other words, the asymmetry of the areas 60, 70 are equal except for the sign. In other words, if the asymmetry of the area 60 is given by A60, and the asymmetry of the area 70 is given by A70, then A60=−A70.

Any other parameter of the features on the test pattern 50 may be varied in order to make the asymmetry of the first area 60 of the pattern 50 substantially equal in magnitude but opposite in sign to the second area 70. For example, the pitch p1, p2 and/or width q1, q2 of the teeth 66, 76 could be varied.

In order to measure the asymmetry of the two areas 60, 70 of the pattern 50, the structures could be illuminated with a radiation beam. The radiation from the radiation beam would then be scattered by the two areas 60, 70 of the test pattern 50 on the substrate. This scattered radiation could be collected, and from the collected radiation, a value representing the asymmetry of the two areas 60, 70 could be detected and/or calculated. Such illuminating, collecting, and testing/calculating could be performed by an angle-resolved scatterometer, such as those described in relation to FIGS. 3 and 4 above.

In order to achieve this opposite asymmetry, the comb-like structures 64, 74, typically have different duty cycles to the solid lines 62, 72. For example, the duty cycle of the solid lines 62, 72 could be 25%, and the duty cycle of the comb-like structures 64, 74 could be 10%, or vice versa. In general, the duty cycles of the solid lines 62, 72 would differ from the duty cycles of the comb-like structures 64, 74 by at least 50%. More typically, the duty cycles of the solid lines 62, 72 would differ from the duty cycles of the comb-like structures 64, 74 by at least 100%. More typically, the duty cycles of the solid lines 62, 72 would differ from the duty cycles of the comb-like structures 64, 74 by at least 200%. More typically, the duty cycles of the solid lines 62, 72 would differ from the duty cycles of the comb-like structures 64, 74 by at least 500%.

Although the two areas 60, 70 of the test pattern 50 are shown as being solid lines 62, 72 alternating with comb-like structures 64, 74, other structures could be used that have an asymmetry that is equal except for the sign. For example, the teeth 66, 76 could be provided on alternating sides of the respective solid lines 65, 75 in the comb-like structures 64, 74. Furthermore, the teeth 66, 76 provided on the comb-like structure need not be rectangular, as they are shown in FIG. 9. Instead, the teeth could be triangular in shape. Still alternatively, the teeth could have a shape formed by a triangle with the apex removed. The teeth could be trapezoidal, or trapezial in shape. As such, the angle between the teeth 66, 76 and the solid lines 65, 75 to which they are attached could be 90 degrees, less than 90 degrees, or greater than 90 degrees.

Figure 10:
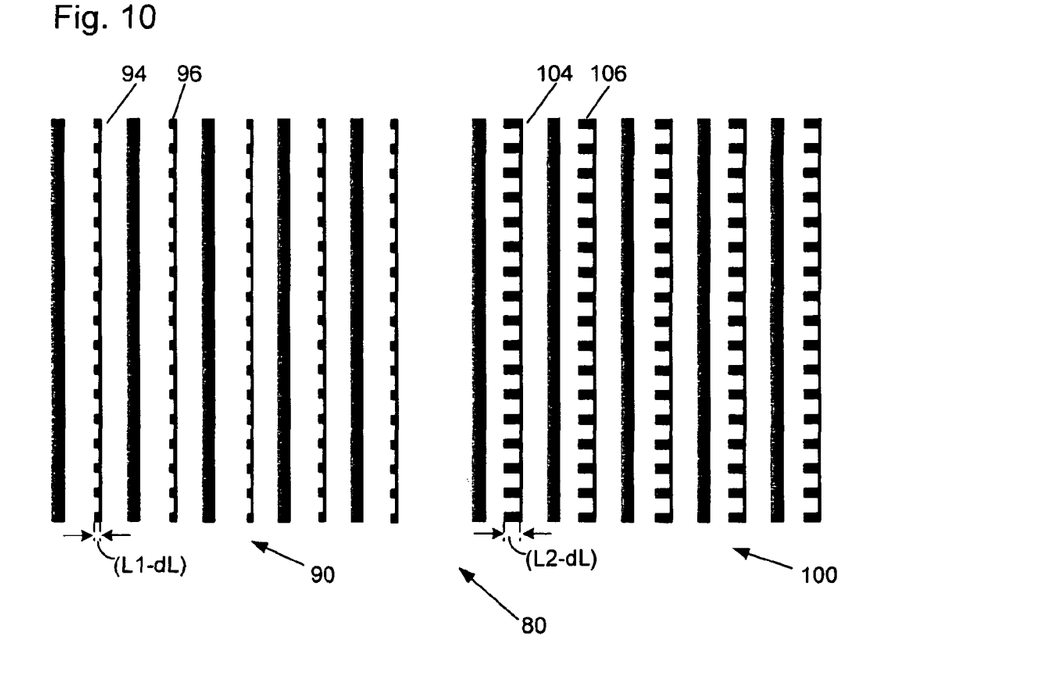
FIG. 10 depicts the pattern shown in FIG. 9 after end of line effects have resulted in line end shortening.

FIG. 10 shows a pattern 80 on a substrate after manufacture. The pattern 80 illustrates how the pattern 50 shown as designed in FIG. 9 may appear after manufacture. As can be seen from FIG. 10, the basic manufactured pattern 80 is the same as the designed pattern 50, but the teeth 96, 106 of the comb-like structures 94, 104 of the manufactured pattern are shorter than the respective teeth 66, 76 of the comb-like structures 64, 74 of the design pattern 50 shown in FIG. 9. This is due to line end shortening that occurs during manufacture, as described above.

Due to the line end shortening of teeth 96, 106 of the manufactured pattern 80, the asymmetry of the two areas 90, 100 of pattern 80 are altered from the corresponding areas 60, 70 in the pattern 50 as designed. Thus, whereas the asymmetry A60 of the first area 60 of the design pattern 50 is equal in magnitude but opposite in sign to the asymmetry A70 of the second area 70 of design pattern 50, the asymmetry A1 of the first area 90 of the manufactured pattern 80 need not be equal in magnitude but opposite in sign to the asymmetry A2 of the second area 100 of the manufactured pattern 80.

The actual asymmetry of the first area 90 and the second area 100 can be measured, for example using angle-resolved scatterometer, as described above. From the measured values A1, A2 of the asymmetry of the manufactured pattern 80, the amount of line shortening of the teeth 96, 106 that has occurred can be calculated or estimated. Because the original test pattern 50 was chosen to represent the typical features of the pattern of interest, the estimated line end shortening of the teeth 96, 106 of the manufactured test pattern 80 can be used to infer, predict, calculate, and/or estimate the line end shortening that would occur to the features of the pattern of interest.

For example, if it is assumed that the difference (L1−L2) between the length L1 of the teeth 66 in the first area 60 of the test pattern 50 as designed and the length L2 of the teeth 76 in the second area 70 of the test pattern as designed is small enough to assume a linear relation (with constant or proportionality K) between the length of tooth and the measured asymmetry for all length of teeth in the design test pattern 50 and the manufactured test pattern 80, then the amount of line end shortening dL can be calculated, as set out below. If the measured asymmetry of the manufactured first area 90 is given by A1, and the measured asymmetry of the second manufactured area 100 is given as A2, then A1 and A2 are given by:

$$A1 = K(0.5(L1+L2)-(L1-dL))$$

$$A2 = K(0.5(L1+L2)-(L2-dL))$$

Eliminating K from these two equations allows for the amount of line end shortening dL to be calculated:

$$dL = \frac{(L1-L2)(A1+A2)}{2(A1-A2)}$$

As stated above, the above equation applies for the case where a linear relationship exists, or is assumed to exist, between the length of the teeth 66, 76, 96, 106 and the measured asymmetry. However, even if such a linear relationship does not exist, then the amount of line end shortening can still be calculated, or estimated, from the measured asymmetry of the manufactured pattern 80. For example, the relationship between the measured asymmetry and the line end shortening could be given by a more complicated relationship (such as a second order relationship), and/or could be calibrated from test patterns of known design and manufactured feature geometry. For example, the actual manufactured geometry of such known test patterns could be established accurately using a scanning electron microscope.

As set out above, the measured asymmetry of a manufactured test pattern can be used in order to calculate and/or estimate the line end shortening of structures on the test pattern. From this, the line end shortening of typical features on a substrate of interest can be inferred, predicted, calculated, and/or estimated. However, the methods and apparatuses described above could also be used to monitor other features. For example, the focus and dose of the radiation used by the lithographic apparatus to manufacture the test pattern could have an affect on the amount of line end shortening that occurs. Thus, the measured asymmetry of the manufactured test pattern 80 could also be used to calculate and/or estimate the focus and dose of the radiation. In the case of using the measured asymmetry to determine the focus error, further analysis of the radiation scattered by the manufactured test pattern may be required in order to determine the sign of the focus error. For example, the effective side wall angle could be used to determine the sign information of the focus error. In order to obtain focus information (for example relating to the sign of the focus error) from the effective side wall angle, the structures in the test pattern would preferably be as spaced apart as possible. Alternatively, a separate, isolated line/structure could be provided with the test pattern to obtain focus information through variations in side wall angle.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method comprising:
    illuminating a test pattern, provided on a substrate, with a radiation beam, the test pattern comprising first and second repeating patterns, wherein:
        the first repeating pattern comprises:
            a first plurality of solid lines, and
            a first plurality of comb-like structures,
        the second repeating pattern comprises:
            a second plurality of solid lines, and
            a second plurality of comb-like structures, and
        a duty cycle of the first or second plurality of solid lines differs from a duty cycle of the first or second plurality of comb-like structures, respectively, by at least 50%;
    measuring radiation scattered by the illuminated test pattern; and
    determining, from the scattered radiation, an amount of line end shortening of a feature on the substrate.

2. The method of claim 1, wherein:
    each comb-like structure of the first and second plurality of comb-like structures comprise teeth having a length L1 and a length L2, respectively; and
    the lengths L1 and L2 are measured in same direction as widths W1 and W2 of each solid line of the first and second plurality of solid lines, respectively.

3. The method of claim 2, wherein:
    the width W1 is substantially equal to the width W2; and
    the length L1 is different from the length L2.

4. The method of claim 2, wherein the width W1 and the width W2 are both greater than about 125% of the length L1 and the length L2.

5. The method of claim 2, wherein the width W1 and the width W2 are both less than about 75% of the length L1 and less than about 75% of the length L2.

6. The method of claim 1, wherein the illuminating is performed by an angle-resolved scatterometer.

7. A substrate comprising:
    a first repeating pattern and a second repeating pattern, wherein:
        the first repeating pattern comprises:
            a first plurality of solid lines, and
            a first plurality of comb-like structures;
        the second repeating pattern comprises:
            a second plurality of solid lines, and
            a second plurality of comb-like structures; and
        a duty cycle of the first or second plurality of solid lines differs from a duty cycle of the first or second plurality of comb-like structures, respectively, by at least 50%.

8. The substrate according to claim 7, wherein:
    each comb-like structure of the first and second plurality of comb-like structures comprise teeth having a length L1 and a length L2, respectively;
    the lengths L1 and L2 are measured in same direction as widths W1 and W2 of each solid line of the first and second plurality of solid lines, respectively;
    the width W1 is substantially equal to the width W2; and
    the length L1 is different from the length L2.

9. A patterning device comprising:
a pattern configured to be used to form a first repeating pattern and a second repeating pattern on a substrate, wherein:
  the first repeating pattern comprises:
    a first plurality of solid lines, and
    a first plurality of comb-like structures;
  the second repeating pattern comprises:
    a second plurality of solid lines, and
    a second plurality of comb-like structures; and
  a duty cycle of the first or second plurality of solid lines differs from a duty cycle of the first or second plurality of comb-like structures, respectively, by at least 50%.

10. The patterning device according to claim 9, wherein:
each comb-like structure of the first and second plurality of comb-like structures comprise teeth having a length L1 and a length L2, respectively;
the lengths L1 and L2 are measured in same direction as widths W1 and W2 of each solid line of the first and second plurality of solid lines, respectively;
the width W1 is substantially equal to the width W2; and
the length L1 is different from the length L2.

11. A measurement system comprising:
a radiation device configured to irradiate a test pattern on the substrate with a radiation beam;
a detector device configured to detect radiation that has been scattered by the irradiated test pattern,
wherein the test pattern comprises a first repeating pattern and a second repeating pattern, wherein:
  the first repeating pattern comprises:
    a first plurality of solid lines, and
    a first plurality of comb-like structures,
  the second pattern comprises:
    a second plurality of solid lines, and
    a second plurality of comb-like structures, and
  a duty cycle of the first or second plurality of solid lines differs from a duty cycle of the first or second plurality of comb-like structures, respectively, by at least 50%; and
a controller configured to calculate an amount of line end shortening of a feature on the substrate from the detected radiation.

12. The measurement system according to claim 11, wherein:
each comb-like structure of the first and second plurality of comb-like structures comprise teeth having a length L1 and a length L2, respectively;
the lengths L1 and L2 are measured in same direction as widths W1 and W2 of each solid line of the first and second plurality of solid lines, respectively;
the width W1 is substantially equal to the width W2; and
the length L1 is different from the length L2.

13. The measurement system according to claim 11, wherein the radiation device, a collector, and the detector are components of an angle-resolved scatterometer.

* * * * *